US008213568B2

United States Patent
Heuscher et al.

(10) Patent No.: US 8,213,568 B2
(45) Date of Patent: Jul. 3, 2012

(54) DYNAMIC COLLIMATION IN CONE BEAM COMPUTED TOMOGRAPHY TO REDUCE PATIENT EXPOSURE

(75) Inventors: Dominic J. Heuscher, Aurora, OH (US); Felix Godfried Peter Peeters, Heide (NL)

(73) Assignee: Koninklijke Philips Electronics N.V., Eindhoven (NL)

(*) Notice: Subject to any disclaimer, the term of this patent is extended or adjusted under 35 U.S.C. 154(b) by 282 days.

(21) Appl. No.: 12/746,350

(22) PCT Filed: Dec. 12, 2008

(86) PCT No.: PCT/IB2008/055269
§ 371 (c)(1),
(2), (4) Date: Jun. 4, 2010

(87) PCT Pub. No.: WO2009/083850
PCT Pub. Date: Jul. 9, 2009

(65) Prior Publication Data
US 2010/0246752 A1    Sep. 30, 2010

Related U.S. Application Data

(60) Provisional application No. 61/015,784, filed on Dec. 21, 2007.

(51) Int. Cl.
*A61B 6/00* (2006.01)

(52) U.S. Cl. .......................................... 378/15; 378/150
(58) Field of Classification Search ............... 378/4–20, 378/145, 147, 150, 193–198
See application file for complete search history.

(56) References Cited

U.S. PATENT DOCUMENTS

| | | | |
|---|---|---|---|
| 4,969,174 A | 11/1990 | Scheid et al. | 378/145 |
| 5,608,776 A | 3/1997 | Hsieh | 378/146 |
| 6,647,092 B2 | 11/2003 | Eberhard et al. | 378/65 |
| 6,891,919 B2 | 5/2005 | Kresse et al. | 378/19 |
| 7,260,171 B1 | 8/2007 | Arenson et al. | 378/16 |
| 7,508,903 B2 * | 3/2009 | Nishide et al. | 378/15 |
| 2002/0080910 A1 | 6/2002 | Kuroda | |
| 2003/0031290 A1 * | 2/2003 | Sugihara et al. | 378/15 |
| 2007/0116171 A1 | 5/2007 | Hsieh et al. | |

FOREIGN PATENT DOCUMENTS
WO    2005023114 A2    3/2005

* cited by examiner

*Primary Examiner* — Courtney Thomas

(57) ABSTRACT

When performing a fly-by or helical CT scan of a subject, radiation dose is limited by positioning a dynamic collimator (142) between the subject and an X-ray source (112). The collimator moves axially with the X-ray source (112) along a volume of interest (VOI) (122) in the subject and gradually opens, such that a narrow portion of the cone beam of X-rays is permitted to pass through the collimator (142) at ends of the VOI (122) and a wider full cone beam is emitted at central portions of the VOI (122). In this manner, tissue surrounding the VOI (122) is not needlessly exposed to X-rays, as would be the case if a full-width cone beam were used for the entire scan of the VOI (122).

21 Claims, 5 Drawing Sheets

DYNAMIC COLLIMATION IN CONE BEAM COMPUTED TOMOGRAPHY TO REDUCE PATIENT EXPOSURE

CROSS REFERENCE TO RELATED APPLICATIONS

This application claims the benefit of U.S. provisional application Ser. No. 61/015,784 filed Dec. 21, 2007, which is incorporated herein by reference.

DESCRIPTION

The present application relates generally to imaging systems, particularly involving helical computed tomography (CT). However, it will be appreciated that the described technique may also find application in other imaging systems, other medical imaging scenarios, or other image data acquisition techniques.

Conventional cone beam CT systems have included multi-slice detectors, which enable such systems to scan larger regions/volumes of interest in shorter periods of time relative to their single-slice system predecessors. One technique for imaging larger volumes is helical scanning. In helical scanning, the subject moves axially relative to the cone beam such that the cone beam traverses a helical path through the patient. Such scanning can be leveraged to quickly scan whole or large portions of organs and improve temporal resolution.

However, conventional CT systems provide a constant collimated cone beam throughout a scan. At the beginning and end of the helical scan, only a portion of the radiation traverses the reconstructed volume and produces data that is used for reconstruction. The rest of the cone beam irradiates adjacent portions of the subject but provides no data that is used in the reconstruction.

The present application provides new and improved CT scanning systems and methods, which overcome the above-referenced problems and others.

In accordance with one aspect, a system for limiting radiation dose to a patient during a computed tomography scan includes an X-ray source on a rotating gantry configured to move axially parallel to a volume of interest (VOI) on a stationary subject support as the X-ray source rotates around the VOI, a dynamic collimator positioned between the X-ray source and the VOI and moveable with the X-ray source, and an X-ray detector positioned opposite the X-ray source and collimator to receive X-rays that have passed through the VOI. The X-ray source begins CT acquisition of the VOI at an X-ray initiation position, terminates CT acquisition of the VOI at an X-ray termination position. The dynamic collimator begins to open at the X-ray initiation position to limit X-rays passing through the collimator to X-rays that will pass through the VOI, opens in coordination with axial movement to permit a full X-ray cone beam to pass through to scan the VOI, and closes in coordination with axial movement to reduce X-rays passing through the collimator as the collimator approaches the X-ray termination position.

In accordance with another aspect, a method of reducing radiation dose to a subject during a CT scan includes starting axial movement of an X-ray source and a dynamic collimator at a start point, initiating CT acquisition by the X-ray source at an X-ray initiation position, and opening shutter blades on the dynamic collimator at the X-ray initiation position to permit a portion of an X-ray cone beam that passes through a VOI (, and to block a portion of the X-ray cone beam that does not pass through the VOI. The method further includes increasing at least an axial width of the X-ray cone beam until the VOI is exposed to a full X-ray cone beam, as the X-ray source and dynamic collimator move axially toward a midpoint of the VOI, and reducing at least an axial width of the X-ray cone beam as the X-ray source and dynamic collimator move axially away from the midpoint of the VOI, toward an X-ray termination position, wherein the dynamic collimator blocks X-rays that will not pass through the VOI.

In accordance with another aspect, a method of scanning a VOI includes moving a cone beam of radiation from a first end of the VOI to a second end along a substantially helical path, truncating a trailing portion of the cone beam adjacent the first end of the VOI, and truncating a leading portion of the cone beam adjacent the second end of the VOI.

In accordance with another aspect, a system for controlling radiation during a CT scan includes a dynamic collimator, coupled to an X-ray source and positioned between the X-ray source and a VOI, and that moves axially along, and rotationally around, the VOI along a helical path, and a first axially stationary collimator positioned between the an X-ray initiation position and a first end the VOI to limit a portion of a cone beam of radiation passing from the X-ray source through the dynamic collimator to X-rays that pass through the VOI. The system further includes a second axially stationary collimator positioned between an X-ray termination position and a second end the VOI to limit a portion of the cone beam passing from the X-ray source through the dynamic collimator to X-rays that pass through the VOI.

In accordance with another aspect, a system that facilitates limiting radiation dose received by a subject during a tilted axis CT scan includes an X-ray source that rotates around a VOI while moving axially along the VOI, and a dynamic collimator coupled to the X-ray source and positioned between, and rotatable with, the X-ray source around the VOI. The dynamic collimator opens to emit a tilted-axis X-ray cone beam while limiting X-ray emission through the dynamic collimator to only X-rays that pass through the VOI and are usable for image reconstruction of the VOI.

One advantage is that X-ray dose to a patient is minimized

Still further advantages of the subject innovation will be appreciated by those of ordinary skill in the art upon reading and understand the following detailed description.

The innovation may take form in various components and arrangements of components, and in various steps and arrangements of steps. The drawings are only for purposes of illustrating various aspects and are not to be construed as limiting the invention.

FIG. 3 shows another embodiment of the system, wherein the dynamic collimator moves with the X-ray source and maintains a constant aperture size for letting X-rays generated by the source pass through.

Systems and methods are described below that relate to a fly-by CT scanner, although they are applicable any type of helical CT scanner. During a helical CT scan, an X-ray source generates a cone (or wedge) beam of radiation that moves relative to the patient. Toward the ends of the scan, portions of the cone beam of radiation typically do not pass through the volume to be reconstructed. While this extra radiation has no adverse effect on the reconstructed image, it does subject the patient to more radiation than is necessary. Accordingly, various embodiments described herein relate to replacing a conventional fixed collimator with a dynamically adjustable collimator. The dynamic collimator is controlled by an electromechanical servo system (e.g., a controller) and an electronic control that is responsive to a sensor for sensing the axial position of the X-ray source relative to the reconstructed volume. As the X-ray source approaches one end of the travel, the collimator is adjusted to narrow the cone beam and block any extraneous rays of radiation which either will not intersect the volume to be reconstructed or which will intersect a fully sampled portion of the volume of interest.

Figure 1:
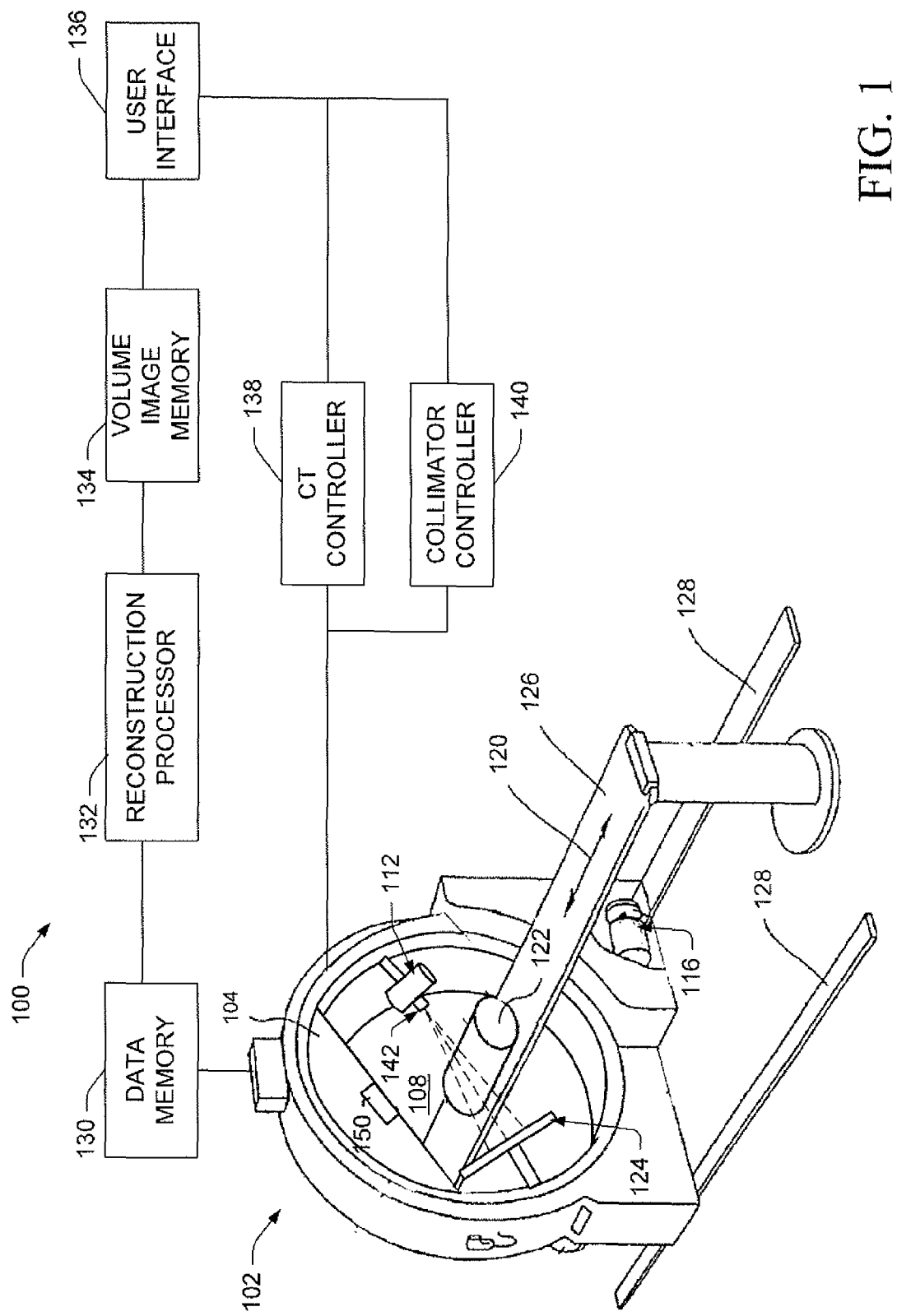
FIG. 1 illustrates a CT imaging system includes a CT scanner with a rotating gantry portion that rotates about an examination region.

With reference to FIG. 1, a CT imaging system 100 includes a CT scanner 102 with a rotating gantry portion 104 that rotates about an examination region 108 and moves axially there along. The rotating gantry portion 104 supports an x-ray source 112, e.g., an X-ray tube, which radiates a cone or wedge X-ray beam that is collimated to have a generally conical geometry. A drive mechanism 116 moves the x-ray source longitudinally along a z-axis 120. In one implementation, the motion of the x-ray source and emission of radiation thereby are coordinated to scan a volume of interest (VOI) 122 such as anatomy disposed within the examination region 108 which is optionally enhanced with a contrast agent. As described below, such coordination can be used for fly-by scanning, for example. In one embodiment, the X-ray source and detector move in coordination with a contrast agent through the subject such that the VOI is scanned in coordination with the flow of the agent as it is traced through the VOI. In another embodiment, the axial advancement is coordinated with a motion of the subject to capture a desired motion state.

The rotating gantry portion 104 also supports an x-ray sensitive detector array 124, which is disposed about the rotating gantry portion 104 disposed opposite the x-ray source 112. The detector array 124 includes a multi-slice detector having a plurality of detector elements extending in the axial and transverse directions. Each detector element detects radiation emitted by the x-ray source 112 that traverses the examination region 108 and generates corresponding output signals or projection data indicative of the detected radiation. Rather than being arranged in a third generation configuration, other configurations, such as fourth generation configurations in which stationary detectors surround the examination region, are also contemplated herein.

The CT imaging system 100 further includes a couch or patient support 126 that supports a subject, such as a human patient in which the VOI is defined within the examination region 108. The support 126 is stationary while the rotating gantry 104 is axially movable along tracks 128 that run parallel to the axis 120, which enables an operator of the system to suitably define the VOI to encompass the whole subject or a portion thereof for scanning. In one embodiment, the CT scanner performs a helical scan of the VOI by rotating around the axis 120 as the gantry is moved axially parallel to the axis.

The projection data generated by the detector array 124 is stored to a data memory 130 and processed by a reconstruction processor or means 132, which reconstructs the projections and generates a volumetric image representation therefrom. The reconstructed image data is stored in a volume image memory 134 and displayed to a user via a user interface 136. The image data is processed to generate one or more images of the scanned region of interest or a subset thereof.

The user interface 136 facilitates user interaction with the scanner 102.

Software applications executed by the user interface 136 allow the user to configure and/or control operation of the scanner 102. For instance, the user can interact with the user interface 136 to select scan protocols, and initiate, pause and terminate scanning. The user interface 136 also allows the user to view images, manipulate the data, measure various characteristics of the data (e.g., CT number, noise, etc.), etc.

An optional physiological monitor (not shown) monitors cardiac, respiratory, or other motion of the VOI. In one example, the monitor includes an electrocardiogram (ECG) or other device that monitors the electrical activity of the heart. This information is used to trigger one or more fly-by scans or to synchronize fly-by scanning with the heart electrical activity. An optional injector (not shown) or the like is used to introduce agents such as contrast into the subject. Likewise, the introduction of the agent can be used to trigger one or more fly-by scans.

The system 100 further includes a CT controller 138, which controls rotational and axial movement of the X-ray source 112 and the X-ray detector 124. The CT scanner and CT controller are additionally coupled to a collimator controller 140 that controls movement, and opening and closing, of a collimator 142 positioned between the X-ray source and the examination region 108. In one embodiment, the collimator controller causes the collimator to function as a shutter to block radiation between scans and to open at a predefined rate as the rotatable gantry 104 (and accordingly the source 112 and detector 124 coupled thereto) starts moving axially along the VOI 122 at the beginning of a scan. In one embodiment, the collimator controller 140 includes an electro-mechanical servo motor. In another embodiment, the collimator controller 140 includes an electronic controller. By gradually opening the collimator 142, the leading end of the VOI and adjacent regions receives less than a full cone beam of X-rays, thereby reducing the X-ray dose. As the source moves along the patient, the collimator is opened further, widening the full cone beam to ensure coverage of the VOI. As the source approaches the trailing end of the VOI, the collimator closes at a predetermined rate relative to the speed of axial movement to limit the X-ray dose received by the patient while ensuring collection of sufficient scan data.

In another embodiment, control of the collimator aperture is not governed by a predetermined rate of opening or closing, but rather by a sensed position of the source 112 relative to the VOI. That is, when the source is near or approaching an end of the VOI during a scan, the collimator aperture can be reduced to limit the X-ray dose to the VOI. In this embodiment, the CT scanner 102 can include suitable sensors 150 (e.g., infrared sensors, camera sensors, etc.) to detect VOI position.

Figure 2:
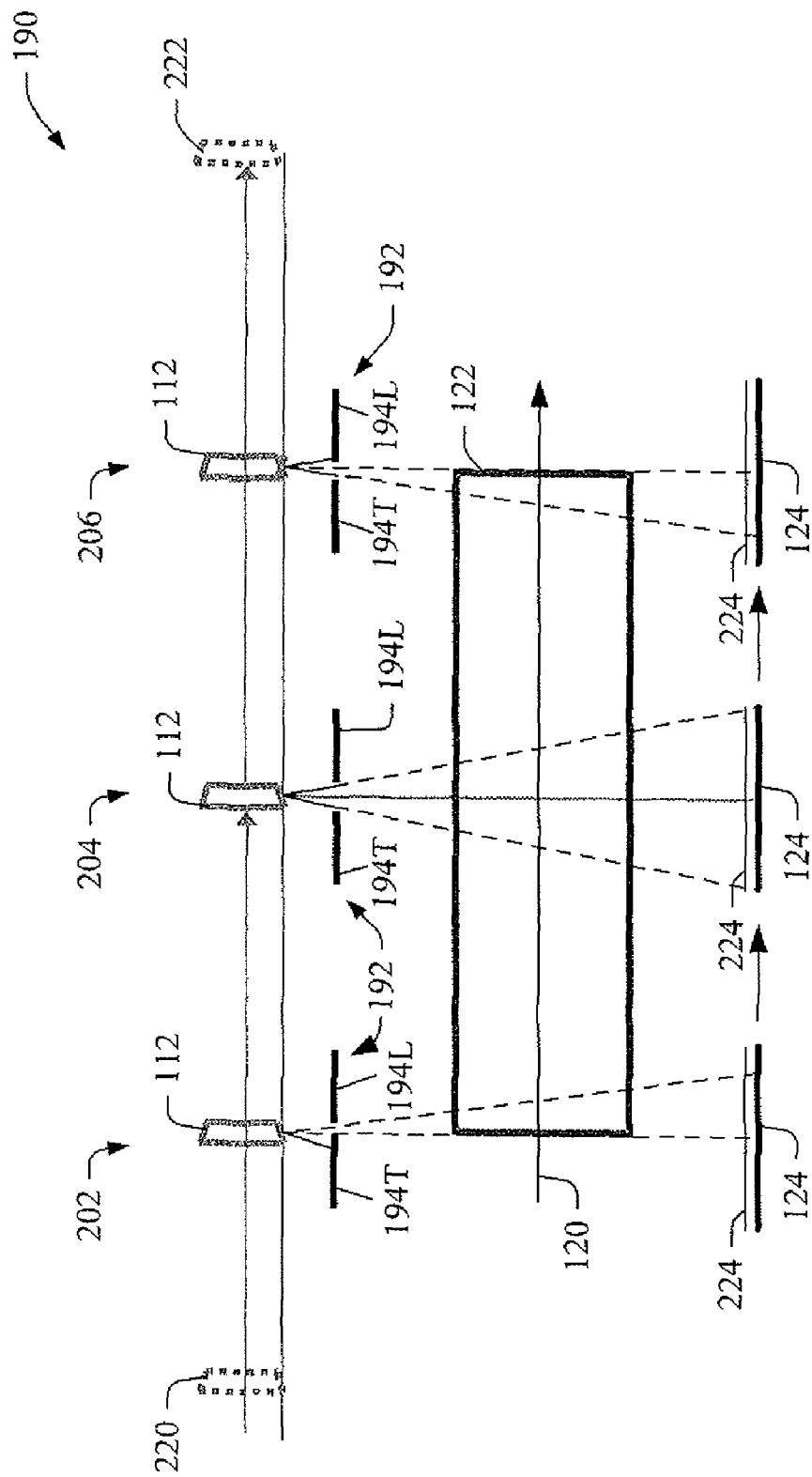
FIG. 2 illustrates a system including a dynamic collimator synchronized to the motion of the axial X-ray source, such as occurs in a fly-by scan in which a subject support is stationary and the source (or the source/detector combination) moves axially to cover the VOI.

FIG. 2 illustrates a system 190 including a dynamic collimator 142 synchronized to the motion of the axial X-ray source 112, such as occurs in a fly-by scan in which a subject support (FIG. 1) is stationary and the source 112 (or the source 112/detector 124 combination) moves axially to cover the VOI 122. The collimator includes at least two high-speed shutter or collimator blades 194 that are independently adjustable to define a collimator aperture through which X-rays are permitted to pass. The collimator can be fixed to a rotate plate on the CT scanner gantry or attached to the source 112 itself. The collimator 142, the source 112, and the detector 124 are illustrated in several positions 202, 204, 206 along the volume of interest. The movement of the source/detector combination defines a helical beam trajectory around the stationary support. The source motion profile defines the motion of the dynamic collimator 142. In this manner, excess radiation is reduced at the beginning and end of a scan in which the source or source/detector combination moves to define the X-ray beam trajectory, as in a fly-by scan. The dynamic collimator limits the radiation at either end of the scan to a minimum amount to reconstruct the volume of interest. Additionally, motion profiles can include trajectories for scan types including helical, fly-by, saddle, etc.

In one embodiment, the collimator 142 is attached to the source 112. In another embodiment, such as where the collimator is positioned close to the volume of interest, the collimator 142 may be separate from the source 112. In this manner, the collimator reduces X-ray dose to the patient by blocking any unused or unnecessary x-rays (e.g., X-rays that do not pass through the volume of interest) and allowing only those x-rays used for reconstruction to pass through.

The collimator 142 is closed at the beginning of the scan until the x-ray source 112 has accelerated to its rotational speed, e.g., 240 rpm or higher. The collimator then opens up such that all rays that are used by the reconstruction at the beginning of the scan are permitted to pass through the collimator. The collimator opens fully until approaching the end of the scan. As the collimator approaches the end of the field of view, it closes in coordination with the axial motion to allow only those X-rays to pass that are required for reconstruction of the end of the scan. The collimator is fully closed and the source can stop emitting X-rays and decelerate to a stopped position.

If the collimator is attached to the rotate plate (not shown) of the gantry, as in a scenario where the collimator is in close proximity to the patient, a shutter is typically connected with the source. As the scan begins, a trailing blade 194T, which is initially closed, gradually opens the collimator aperture as the scan proceeds, to allow only those X-rays required for reconstruction to pass through. That is, the trailing blade truncates a trailing portion of the cone beam to block radiation that does not intersect the selected VOI. If a fixed collimator is attached to the source to define the full extent of the cone-beam, then the dynamic collimator can stop narrowing the collimator aperture as the scan proceeds through a midsection of the volume of interest. Symmetrical motion then occurs for a leading blade 194L as the source approaches the end of the VOI. The leading blade moves toward the trailing blade to truncate a leading portion of the cone beam that would not pass through the VOI.

In one embodiment, the X-ray source 112 and collimator 192 start at a start position 220 and accelerate to a predetermined velocity parallel to the z-axis 120 before CT acquisition begins at the first position 202 (e.g., an X-ray initiation position, where scanning of the VOI is started). The collimator opens from the trailing side at or just prior to the first position 202, and opens to a fully-open state by the time it reaches the second position 204. The collimator then begins closing from the leading side as it approaches position 206 to reduce the width of the cone beam emitted by the X-ray source 112. The collimator and X-ray source then decelerate during travel to an end position 222, where the collimator and X-ray source come to rest. Alternatively, a further scan can be started immediately in the return direction to continue imaging the VOI. It will be appreciated that the X-ray detector can be a stationary (e.g., axially and/or rotationally) X-ray detector or can be movable to travel with the X-ray source and collimator along the volume of interest parallel to the z-axis. In the case of a moveable detector, an anti-scatter grid 224 can be employed to improve image reconstruction quality and reduce radiation dose to the patient.

According to an example, the system 190 is employed to provide dynamic collimation for a fly-by scan of the volume of interest. For example, a wide-angle cone beam and a wide detector, e.g., 500-1000 slices, are sized to generate a full set of data in approximately one revolution with a very coarse-pitch helix. The distance between position 202 and position 206 can be approximately 40 cm, although smaller or greater distances of X-ray travel are contemplated.

In another example, the collimator and X-ray source travel parallel to the Z-axis while rotating around the VOI 122. The collimator opens during travel along predefined arcs along the circumference of rotation, and is closed while travelling other portions of the circumference. For instance, the collimator can be open for a 30° arc and then closed for a 45° arc, in order to facilitate acquiring overlapping scan data of the patient without continuously irradiating the patient. In this manner, X-ray dose to a patient can be limited when using a high-speed rotating CT scanner that makes several revolutions around the patient during the traversal of the z-axis.

FIG. 2 thus illustrates exemplary motion of the X-ray source 112 along the z-direction and corresponding X-ray beam geometry. In this example, the X-ray source 112 is shown moving from a first position 202, through a second position 204, to a third position 206. While translating between the first and third positions 202 and 206, the X-ray source 112 rotates around the examination region (FIG. 1) and emits X-rays. The X-ray source 112 may also move from the third position 206, through the second position 204, to the first position 202, for example, when performing the initial or a subsequent scan. Physical movement of the X-ray source 112 extends outside of a region defined by the first and third positions 202 and 206 to allow for accelerating or ramping up the X-ray source to a suitable speed prior to a scan and decelerating or ramping down the X-ray source after the scan.

While accelerating to its full rotational speed, the X-ray source remains at the location outside of the position 202 (or 206) along the z-axis. After the X-ray source then ramps up to a suitable scanning speed, it moves in the direction of the position 206 (or 202). Upon reaching the initial scanning position 202 (or 206), X-rays are emitted for a sampling period in which complete sampling for a 180 degree reconstruction for each voxel throughout the volume is performed. It is to be appreciated that the X-ray source can move at a constant or a variable speed. Upon reaching the position 206 (or 202), the X-ray source decelerates to another location outside of the positions 206 (or 202). In another embodiment, the X-ray source reverses direction along the z-axis and continues scanning in the opposite direction.

The geometry of the cone beam is defined by the collimator 142, also shown at positions 202, 204, and 206. The collimator 142 moves with a variable collimation (e.g., variable collimator aperture size) in coordination with the movement of the x-ray source 112. As illustrated, the collimator has a narrow aperture and is offset at position 202 to direct a narrow cone beam at a portion of the VOI 122 without exposing the VOI to extraneous radiation. At position 204, the collimator is fully open to permit a wide cone beam to pass through to the VOI. At position 206, the collimator has again narrowed the aperture to permit only X-rays needed for reconstruction to pass through the aperture.

Figure 3:
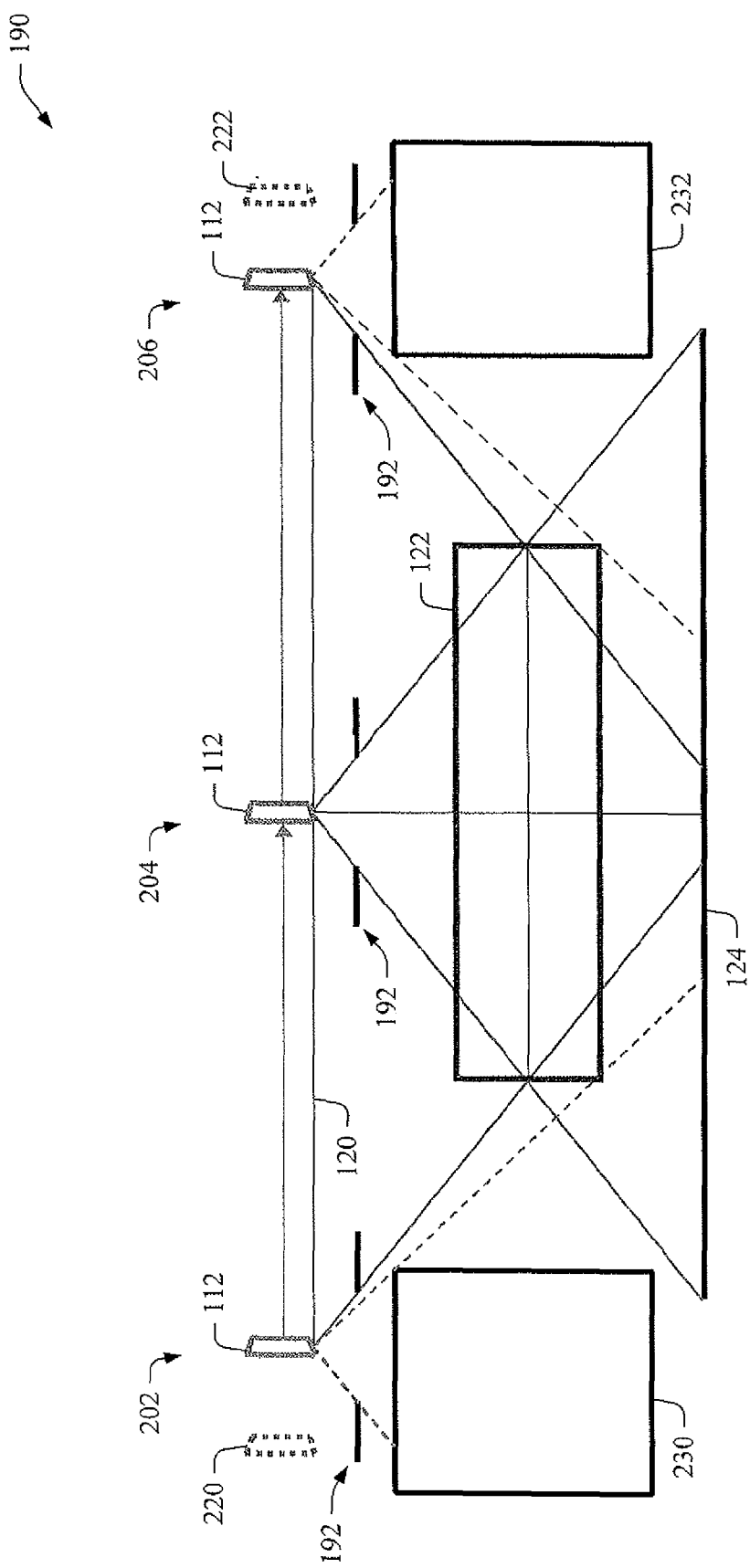

FIG. 3 shows another embodiment of the system 190, wherein the dynamic collimator 142 moves with the X-ray source 112 and maintains a constant aperture size for letting X-rays generated by the source 112 pass through. In one embodiment, collimators 230, 232 are cylindrical, in which case they are stationary both axially and rotationally. In another embodiment, the collimators 230, 232 are substantially flat and are stationary relative to the z-axis, but rotate with the X-ray source. Stationary cylindrical collimators 230, 232 at opposing ends of the travel path of the source and dynamic collimator limit X-ray exposure to the VOI 122 at the ends thereof. The stationary collimators 230 and 232 are located approximately at positions 202 and 206, respectively, along the z-axis 120. The stationary collimators are positioned to filter or block portions of the X-ray beam as the X-ray source 112 approaches the first and third positions 202 and 206, and are configured to collimate the X-ray beam so that the X-ray beam irradiates the VOI 122 as the X-ray source 112 moves between the first and third positions 202 and 206 while rotating around the VOI. More specifically, the stationary detector is positioned to truncate the portion of the cone beam that does not intersect the VOI. This configuration provides complete sampling. Radiation exposure to the patient or VOI by X-rays traversing paths outside of the region of interest 120 is reduced by blocking portions of the X-ray beam by the collimators 230 and 232 so that outer projections and of the X-ray beam illuminating the detector array 124 respectively cross corners and of the VOI 122.

In one embodiment, the X-ray source 112 and collimator 192 start at a start position 220 and accelerate to a predetermined velocity parallel to the z-axis 120 before initiating X-ray emission at the first position 202 (e.g., the X-ray initiation position, where CT scanning of the VOI begins). The collimator 192 maintains a constant aperture during travel from the X-ray initiation position 202 to the third position 206 (e.g., an X-ray termination position where scanning of the VOI in a given direction ends). The collimator 192 and X-ray source then decelerate during travel to an end position 222, where the collimator 192 and X-ray source come to rest. It will be appreciated that the X-ray detector can be a stationary, cylindrical X-ray detector, or can be movable to travel with the X-ray source and collimator along the volume of interest parallel to the z-axis. That is, in one embodiment, the detector is cylindrical, in which case it is stationary both axially and rotationally. In another embodiment, the detector is a substantially flat detector that is axially stationary and rotates with the X-ray source and collimator to maintain an approximately 180° orientation relative thereto.

Figure 4:
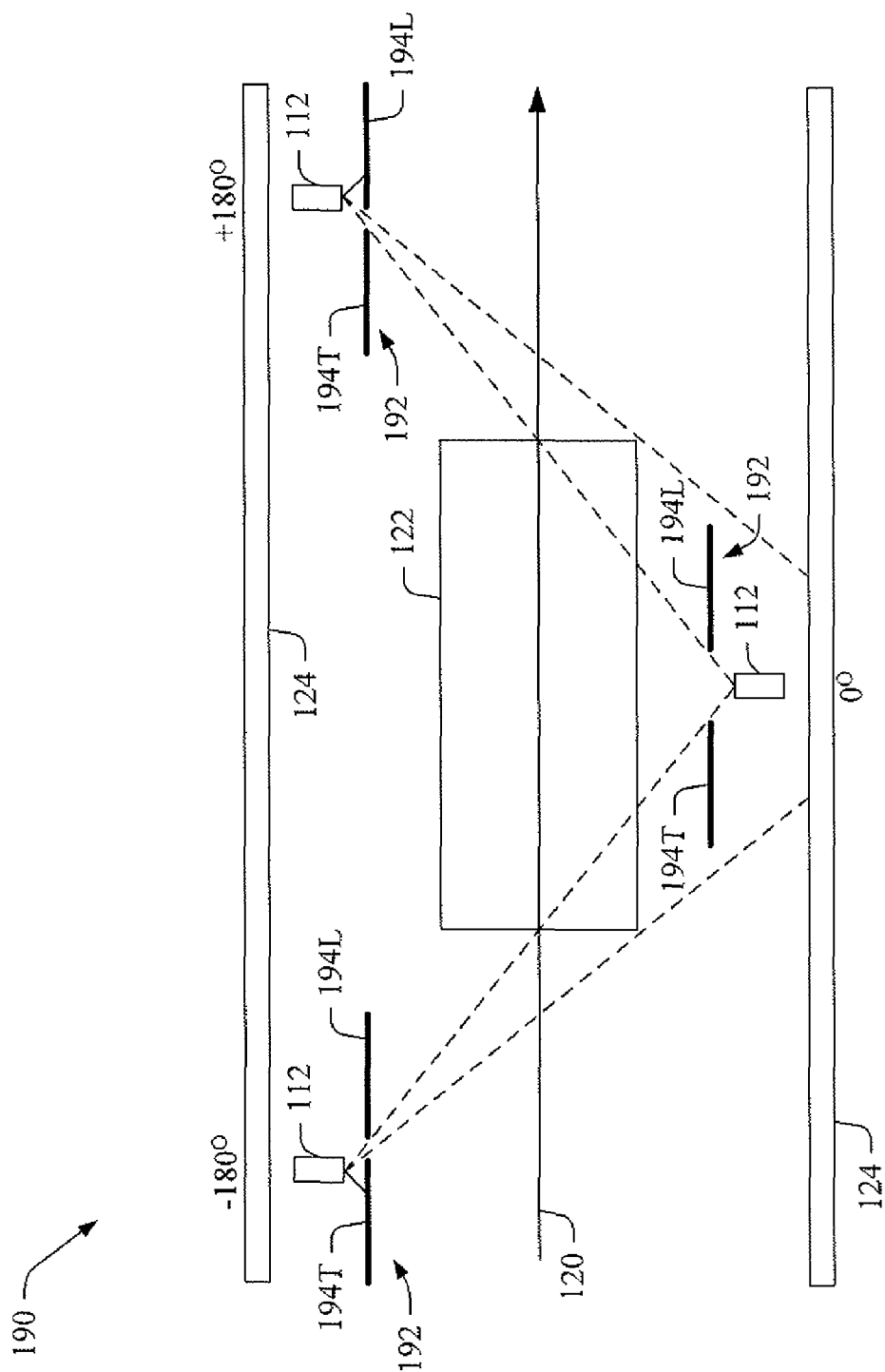
FIG. 4 illustrates a 1+ revolution embodiment with a stationary cylindrical detector.

FIG. 4 illustrates a 1+ revolution embodiment with a stationary cylindrical detector 124. At a center of the scan, the source 112 is located at a position, arbitrarily denoted as 0°. At 0°, the collimator 142 is fully open to define a radiation beam just spans the VOI 122 on its center axis 120. As the source 112 rotates past the 0° position toward a +180° position, the leading collimator blade 194L starts to move toward the trailing collimator blade 194T such that a leading ray of the cone beam is just tangent to a corner of the VOI. At the +180° position, the trailing edge of the cone beam intersects the end of the VOI at the center axis and the leading edge of the cone beam still intersects the corner of the VOI. The source rotates a few degrees past the +180° position until only a single slice of the cone beam intersects the corner of the VOI. During these few degrees of travel, the collimator 142 narrows the cone beam in the transverse direction, such that the width of the cone beam just spans the intersected portion of the cylindrical VOI. In this manner, the cone beam narrows to a single ray as it narrows in the axial direction to a single slice. That is, the cone beam narrows to a single ray at the end of the VOI.

Analogously, approaching a −180° position, the cone beam starts as a singly ray and widens in both dimensions. At the −180° position, the cone beam has its full traversal width. The axial width continues to increase until the source reaches the 0° position.

In other embodiments, other pitches of helical trajectories and other cone beam widths are also contemplated.

Figure 5:
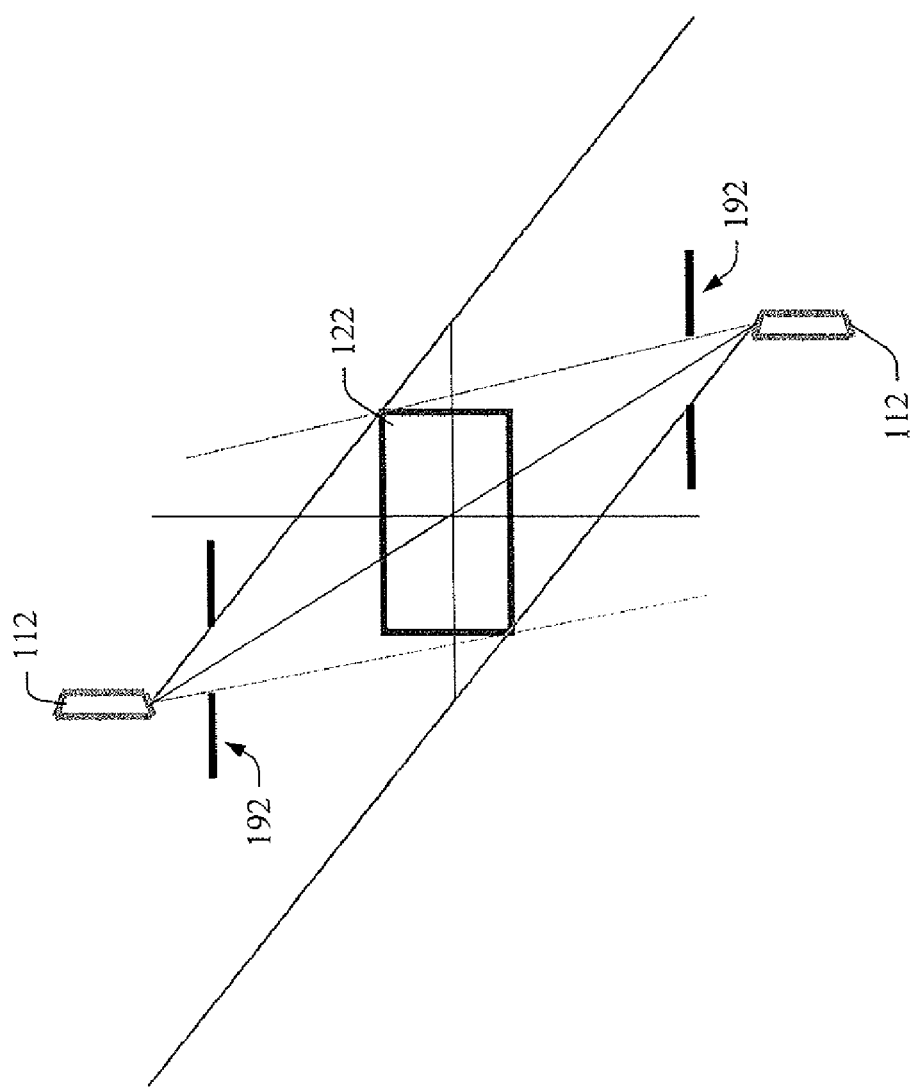
FIG. 5 illustrates an embodiment in which the system is employed to perform tilted-beam collimation for an axial scan.

FIG. 5 illustrates an embodiment in which the system 190 is employed to perform tilted-beam collimation for an axial scan.

An X-ray source 112 and collimator 142 are illustrates in 180° opposing orientations, as the X-ray source and collimator rotate around the VOI 122. For example, the X-ray source can start at one end of the VOI and move along the z-axis as it rotates around the VOI in a helical trajectory. Additionally, the collimator 142 can be dynamically adjusted to maintain the X-ray cone beam at a constant or variable size, while intersecting the VOI 122 without permitting extraneous X-rays (e.g., X-rays that will not traverse the VOI or be used for reconstruction) to pass through the collimator 142. That is, the collimator moves with the X-ray source to generate a tilted cone beam field of view, which rotates around the VOI as the source and collimator travel axially along the VOI. The collimator aperture can be adjusted to compensate for slight variations in magnification due to the tilt of the cone beam.

The innovation has been described with reference to several embodiments. Modifications and alterations may occur to others upon reading and understanding the preceding detailed description. It is intended that the innovation be construed as including all such modifications and alterations insofar as they come within the scope of the appended claims or the equivalents thereof.

Having thus described the preferred embodiments, the invention is now claimed to be:

1. A system for limiting radiation dose to a patient during a computed tomography scan, including:
   an X-ray source on a rotating gantry configured to move axially parallel to a volume of interest (VOI) on a stationary subject support as the X-ray source rotates around the VOI;
   a dynamic collimator positioned between the X-ray source and the VOI and moveable with the X-ray source; and
   an X-ray detector positioned opposite the X-ray source and collimator to receive X-rays that have passed through the VOI;
   wherein the X-ray source begins CT acquisition of the VOI at an X-ray initiation position, terminates CT acquisition of the VOI at an X-ray termination position;
   wherein the dynamic collimator begins to open at the X-ray initiation position to limit X-rays passing through the collimator to X-rays that will pass through the VOI, opens in coordination with axial movement to permit a full X-ray cone beam to pass through to scan the VOI, and closes in coordination with axial movement to reduce X-rays passing through the collimator as the collimator approaches the X-ray termination position.

2. The system according to claim 1, wherein the collimator is attached to a rotator plate on a rotatable gantry to which the X-ray source is attached.

3. The system according to claim 1, wherein the collimator is coupled to the X-ray source.

4. The system according to claim 1, wherein the X-ray detector is mounted stationary relative to the gantry, such that as the X-ray source and collimator rotate and move axially parallel to a z-axis through the VOI the detector remains axially stationary.

5. The system according to claim 4, wherein the X-ray detector is mounted to the gantry to be axially movable with the X-ray source and the collimator, and wherein the gantry rotates as the X-ray source, collimator, and X-ray detector move axially parallel to a z-axis through the VOI to perform a helical CT scan.

6. The system according to claim 1, wherein the gantry is configured to move back and forth along the z-axis to scan the VOI alternately in both directions.

7. The system according to claim 1, further comprising:
a sensor that senses a relative position of the VOI and the X-ray source; and
a collimator controller that controls an aperture size of the collimator as a function of the relative position of the VOI and the X-ray source.

8. The system according to claim 1, wherein the dynamic collimator includes shutter blades that are fully opened at the X-ray initiation position, and wherein a full X-ray cone beam emitted through the dynamic collimator at an end of the VOI is limited by an axially stationary, rotatable collimator between the dynamic collimator and the VOI.

9. The system according to claim 1, wherein a full X-ray cone beam emitted through the dynamic collimator at an end of the VOI is limited by a stationary collimator that is cylindrical, and is both axially and rotationally stationary.

10. A method of reducing radiation dose to a subject using the system of claim 1, including:
starting axial movement of the X-ray source and the dynamic collimator at a start point;
initiation CT acquisition by the X-ray source at the X-ray initiation position;
opening shutter blades on the collimator at the X-ray initiation position to permit a portion of an X-ray cone beam that passes through the VOI, and to block a portion of the X-ray cone beam that does not pass through the VOI;
increasing at least an axial width of the X-ray cone beam until the VOI is exposed to a full X-ray cone beam, as the X-ray source and collimator move axially toward a midpoint of the VOI; and
reducing at least an axial width of the X-ray cone beam as the X-ray source and collimator move axially away from the midpoint of the VOI, toward the X-ray termination position.

11. A method of reducing radiation dose to a subject during a CT scan, including:
starting axial movement of an X-ray source and a dynamic collimator at a start point;
initiating CT acquisition by the X-ray source at an X-ray initiation position;
opening shutter blades on the dynamic collimator at the X-ray initiation position to permit a portion of an X-ray cone beam that passes through a VOI, and to block a portion of the X-ray cone beam that does not pass through the VOI;
increasing at least an axial width of the X-ray cone beam until the VOI is exposed to a full X-ray cone beam, as the X-ray source and dynamic collimator move axially toward a midpoint of the VOI; and
reducing at least an axial width of the X-ray cone beam as the X-ray source and dynamic collimator move axially away from the midpoint of the VOI, toward an X-ray termination position, wherein the dynamic collimator blocks X-rays that will not pass through the VOI.

12. The method according to claim 11, further including:
moving a trailing shutter blade away from a leading shutter blade until the full X-ray cone beam is obtained as the dynamic collimator and X-ray source move from the X-ray initiation position toward the midpoint of the VOI; and
moving the leading shutter blade toward the trailing shutter blade to narrow the X-ray cone beam as the dynamic collimator and X-ray source move toward the X-ray termination position.

13. The method according to claim 11, further including:
decreasing the transverse width of the X-ray cone beam as it moves toward the X-ray termination position.

14. The method according to claim 11, further including:
moving the cone beam back and forth between the X-ray initiation position and the X-ray termination position.

15. A method of scanning a VOI, comprising:
moving a cone beam of radiation from a first end of the VOI to a second end along a substantially helical path;
truncating a trailing portion of the cone beam adjacent the first end of the VOI; and
truncating a leading portion of the cone beam adjacent the second end of the VOI.

16. The method according to claim 15, further including:
truncating a transverse width of the cone beam adjacent to the first and second ends of the VOI.

17. A CT system including a collimator and collimator control processor programmed to perform the method of claim 15.

18. A collimator control processor programmed to control at least one shutter in a collimator to perform the method of claim 15.

19. A system for controlling radiation during a CT scan, including:
a dynamic collimator, coupled to an X-ray source and positioned between the X-ray source and a VOI, and that moves axially along, and rotationally around, the VOI along a helical path;
a first axially stationary collimator positioned between the an X-ray initiation position and a first end the VOI to limit a portion of a cone beam of radiation passing from the X-ray source through the dynamic collimator to X-rays that pass through the VOI; and
a second axially stationary collimator positioned between an X-ray termination position and a second end the VOI to limit a portion of the cone beam passing from the X-ray source through the dynamic collimator to X-rays that pass through the VOI.

20. The system according to claim 19, wherein the dynamic collimator comprises a leading shutter blade and a trailing shutter blade that open to permit a full X-ray cone beam to pass through the dynamic collimator, the leading shutter blade truncates an axial-position-dependent leading portion of the cone beam adjacent the second end of the VOI, the trailing shutter blade truncates an axial-position-dependent trailing portion of the cone beam adjacent the first end of the VOI.

21. A system that facilitates limiting radiation dose received by a subject during a tilted axis CT scan, including:
an X-ray source that rotates around a VOI while moving axially along the VOI; and
a dynamic collimator coupled to the X-ray source and positioned between, and rotatable with, the X-ray source around the VOI;
wherein the dynamic collimator opens to emit a tilted-axis X-ray cone beam while limiting X-ray emission through the dynamic collimator to only X-rays that pass through the VOI and are usable for image reconstruction of the VOI.

* * * * *